United States Patent
Prusiner et al.

(10) Patent No.: US 6,331,296 B1
(45) Date of Patent: Dec. 18, 2001

(54) FOOD ADDITIVES WHICH AFFECT CONFORMATIONALLY ALTERED PROTEINS

(76) Inventors: Stanley B. Prusiner, 400 Pacheco St., San Francisco, CA (US) 94116; Surachai Supattapone, 225 Buckingham Way #702, San Francisco, CA (US) 94132; Michael R. Scott, 1200 Clayton St., #9, San Francisco, CA (US) 94114

( * ) Notice: Subject to any disclaimer, the term of this patent is extended or adjusted under 35 U.S.C. 154(b) by 0 days.

(21) Appl. No.: 09/447,456

(22) Filed: Nov. 22, 1999

Related U.S. Application Data

(63) Continuation-in-part of application No. 09/322,903, filed on Jun. 1, 1999, now Pat. No. 6,214,366.

(51) Int. Cl.[7] .................................................. A01N 25/10
(52) U.S. Cl. ................................... 424/78.08; 424/78.17; 424/78.18; 424/78.27; 424/78.31; 424/78.32; 424/405; 424/439; 424/442; 424/438; 424/78.33; 424/78.34; 424/78.35; 426/271; 426/532; 525/512; 525/513; 525/514; 523/122
(58) Field of Search .................. 424/DIG. 76, 78.32, 424/78.35–78.38, 438–442, 405, 78.08, 78.17, 78.18, 78.27, 78.31; 514/772.3–772.7; 523/122; 525/512–514; 426/271, 286, 326, 335, 532

(56) References Cited

U.S. PATENT DOCUMENTS

| | | |
|---|---|---|
| 4,587,329 | 5/1986 | Tomalia et al. . |
| 5,499,979 | 3/1996 | Wong et al. . |
| 5,547,576 * | 8/1996 | Onishi et al. .......................... 210/500 |
| 5,834,020 * | 11/1998 | Margerum et al. ................... 424/484 |
| 5,919,442 * | 7/1999 | Yin et al. ............................ 424/78.18 |
| 6,150,172 | 11/2000 | Schmerr et al. . |
| 6,190,650 * | 2/2001 | Matthews et al. ................. 424/78.71 |
| 6,197,207 | 3/2001 | Chapman et al. . |
| 6,197,935 | 3/2001 | Doillon et al. . |
| 6,221,614 | 4/2001 | Prusiner et al. . |

OTHER PUBLICATIONS

Basler, Oesch et al. (1986) *Cell* 46:417–428.
C.K. Combs et al, *J Neurosci* 19:928–39 (1999).
Gajdusek (1977) *Science* 197:943–960.
Glenner et al. (1989) *J. Neurol. Sci.* 94:1–28.
Haan et al. (1990) *Clin. Neurol. Neurosurg.* 92(4):305–310.
Hardy (1997) *Trends Neurosci.* 20:154–9.
Kalaria et al. (1995) *Neuroreport* 6:477–80.
Kawai et al. (1993) *Brain Res.* 623:142–6.
Kelly (1996) *Curr Opin Strut Biol* 6(1):11–7.
Lai, Colon et al. (1996) *Biochemistry* 35(20):6470–82.
Lendon et al. (1997) *J. Am. Med. Assoc.* 277:825–31.
Mandybur (1989) *Acta Neuropathol.* 78:329–331.
Martin et al. (1994) *Am. J. Pathol.* 145:1348–1381.
Masliah et al. (1996) *J. Neurosci.* 16:5795–5811.
McCutchen, Colon et al. (1993) *Biochemistry* 32(45):12119–27.

(List continued on next page.)

Primary Examiner—Neil S. Levy

(57) ABSTRACT

An assay comprises contacting cells containing a conformationally altered protein with test compound and determining if the altered protein is cleared. The cells may be scrapie-infected neuroblastoma cells. Another assay comprises contacting organ or tissue homogenate (at pH 5.0 or less) with test compound to determine if altered protein in the homogenate is cleared. The homogenate may be brain homogenate from a transgenic mouse infected with human prions. Compounds which are found to clear the altered protein are useful in preventing, arresting and/or reversing (i.e. treating) a disease associated with the conformationally altered protein.

11 Claims, 1 Drawing Sheet

OTHER PUBLICATIONS

McCutchen and Kelly (1993) *Biochem Biophys Res Commun* 197(2) 415–21.

Medori, R., et al. Fatal familial insomnia: a second kindred with mutation of prion protein gene at codon 178. *Neurology* 42, 669–670 (1992).

Miroy, Lai et al. (1996) *Proc. Natl Acad Sci USA* 93(26):15051–6.

Pan, Baldwin et al. (1993) *Proc Natl Acad Sci USA* 90:10962–10966.

Prusiner (1997) The Molecular and Genetic Basis of Neurological Disease, 2nd Edition: 103–143.

Safar, Roller et al. (1993) *J Biol Chem* 268:20276–20284.

Selkoe et al. (1988) *Proc. Natl. Acad. Sci. USA* 85:7341–7345.

Selkoe, (1993) *Trends Neurosci* 16:403–409.

Selkoe (1996) *J. Biol. Chem.* 271:18295–8.

Wilesmith and Wells (1991) *Curr Top Microbiol Immunol* 172:21–38.

Yankner (1996) *Nat. Med.* 2:850–2.

\* cited by examiner

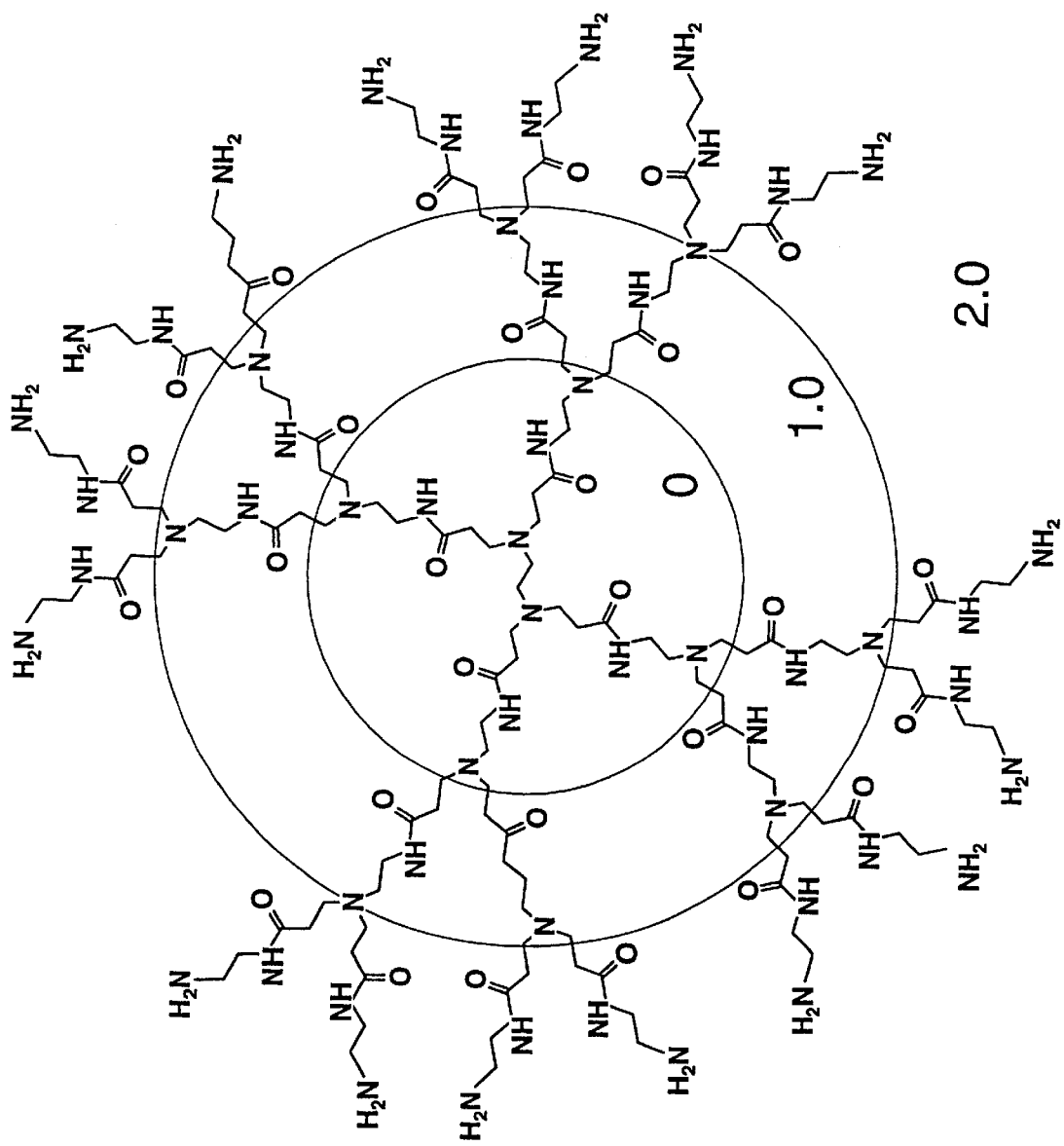

FOOD ADDITIVES WHICH AFFECT CONFORMATIONALLY ALTERED PROTEINS

CROSS-REFERENCES

This application is a continuation-in-part of earlier filed application Ser. No. 09/322,903 filed Jun. 1, 1999 now U.S. Pat. No. 6,214,366 which application is incorporated herein in its entirety and to which application is claimed priority under 35 U.S.C. §120.

GOVERNMENT SUPPORT

This work was supported, in part, by grants from the National Institutes of Health NS14069, AG08967, AG02132, AG10770 and K08 NS02048-02. The government may have certain rights in this work.

FIELD OF THE INVENTION

The present invention relates generally to foods and food additives and specifically to food products which provide a prophylactic affect on conformationally altered proteins associated with disease.

BACKGROUND OF THE INVENTION

There are a number of food products which may be contaminated with conformationally altered proteins. For example, meats and in particular beef and mutton may be contaminated with prions. The problem is particularly difficult to deal with because (1) the animals may be slaughtered before they show any sign of disease; (2) food products are not tested for the presence of prions or other conformationally altered proteins; (3) currently there are no commercially available tests which detect conformationally altered prions; (4) cooking does not destroy conformationally altered proteins; and (5) there are currently no treatments for diseases associated with conformationally altered proteins.

There are a considerable number of diseases associated with a conformationally altered protein. For example, Alzheimer's disease is associated with APP, Aβ peptide, α1-antichymotrypin, tau and non-Aβ component. Many of these diseases are neurological diseases. However, type II Diabetes is associated with Amylin and Multiple myeloma-plasma cell dyscrasias is associated with IgGL-chain. The relationship between the disease onset and the transition from the normal protein to the conformationally altered protein has been examined very closely in some instances such as with the association between prion diseases and $PrP^{Sc}$.

Prion diseases are a group of fatal neurodegenerative disorders that can occur in hereditary, sporadic, and infectious forms (Prusiner, S. B. Scrapie prions. *Annu. Rev. Microbiol.* 43, 345–374 (1989)). These illnesses occur in humans and a variety of other animals (Prusiner, S. B. Prions. *Proc. Natl. Acad. Sci. USA* 95, 13363–13383 (1998)). Prions are infectious proteins. The normal, cellular form of the prion protein (PrP) designated $PrP^C$ contains three α- helices and has little β- sheet; in contrast, the protein of the prions denoted $PrP^{Sc}$ is rich in β-sheet structure. The accumulation of $PrP^{Sc}$ in the central nervous system (CNS) precedes neurologic dysfunction accompanied by neuronal vacuolation and astrocytic gliosis.

The spectrum of human prion diseases includes kuru (Gajdusek, D. C., Gibbs, C. J., Jr. & Alpers, M. Experimental transmission of a kuru-like syndrome to chimpanzees. *Nature* 209, 794–796 (1966)), Creutzfeldt-Jakob disease (CJD) (Gibbs, C. J., Jr., et al. Creutzfeldt-Jakob disease (spongiform encephalopathy): transmission to the chimpanzee. *Science* 161, 388–389 (1968)), Gerstmann-Sträussler-Scheinker disease (GSS) and fatal familial insomnia (FFI) (Goldfarb, L. G., et al. Fatal familial insomnia and familial Creutzfeldt-Jakob disease: disease phenotype determined by a DNA polymorphism. *Science* 258, 806–808 (1992); Medori, R., et al. Fatal familial insomnia: a second kindred with mutation of prion protein gene at codon 178. *Neurology* 42, 669–670 (1992)), and a new form of human prion disease, new variant CJD (nvCJD), which has emerged in Great Britain and France (Will, R. G., et al. A new variant of Creutzfeldt-Jakob disease in the UK. *Lancet* 347, 921–925 (1996); Cousens, S. N., Vynnycky, E., Zeidler, M., Will, R. G. & Smith, P. G. Predicting the CJD epidemic in humans. *Nature* 385, 197–198 (1997); Will, R. G., et al. Deaths from variant Creutzfeldt-Jakob disease. *Lancet* 353, 979 (1999)). Several lines of evidence have suggested a link between the nvCJD outbreak and a preceding epidemic of bovine spongiform encephalopathy (BSE) (Will, R. G., et al. A new variant of Creutzfeldt-Jakob disease in the UK. *Lancet* 347, 921–925 (1996); Bruce, M. E., et al. Transmissions to mice indicate that 'new variant' CJD is caused by the BSE agent. *Nature* 389, 498–501 (1997); Hill, A. F., et al. The same prion strain causes vCJD and BSE. *Nature* 389, 448–450 (1997); Lasmézas, C. I., et al. BSE transmission to macaques. *Nature* 381, 743–744 (1996)). Although it is too early to predict the number of nvCJD cases that might eventually arise in Great Britain and elsewhere (Cousens, S. N., Vynnycky, E., Zeidler, M., Will, R. G. & Smith, P. G. Predicting the CJD epidemic in humans. *Nature* 385, 197–198 (1997)), it is clear that effective therapeutics for prion diseases are urgently needed. Unfortunately, although a number of compounds including amphotericins, sulfated polyanions, Congo red dye, and anthracycline antibiotics have been reported as prospective therapeutic agents (Ingrosso, L., Ladogana, A. & Pocchiari, M. Congo red prolongs the incubation period in scrapie-infected hamsters. *J. Virol.* 69, 506–508 (1995); Tagliavini, F., et al. Effectiveness of anthracycline against experimental prion disease in Syrian hamsters. *Science* 276, 1119–1122 (1997); Masullo, C., Macchi, G., Xi, Y. G. & Pocchiari, M. Failure to ameliorate Creutzfeldt-Jakob disease with amphotericin B therapy. *J Infect. Dis.* 165, 784–785 (1992); Ladogana, A., et al. Sulphate polyanions prolong the incubation period of scrapie-infected hamsters. *J Gen. Virol.* 73, 661–665 (1992)), all have demonstrated only modest potential to impede prion propagation, and none have been shown to effect the removal of pre-existing prions from an infected host.

The PrP gene of mammals expresses a protein which can be the soluble, non-disease form $PrP^C$ or be converted to the insoluble, disease form $PrP^{Sc}$. $PrP^C$ is encoded by a single-copy host gene [Basler, Oesch et al. (1986) Cell 46:417–428] and when $PrP^C$ is expressed it is generally found on the outer surface of neurons. Many lines of evidence indicate that prion diseases result from the transformation of the normal form of prion protein ($PrP^C$) into the abnormal form ($PrP^{Sc}$). There is no detectable difference in the amino acid sequence of the two forms. However, $PrP^{Sc}$ when compared with $PrP^C$ has a conformation with higher β-sheet and lower α-helix content (Pan, Baldwin et al. (1993) *Proc Natl Acad Sci USA* 90:10962–10966; Safar, Roller et al. (1993) *J Biol Chem* 268:20276–20284). The presence of the abnormal $PrP^{Sc}$ form in the brains of infected humans or animals is the only disease-specific diagnostic marker of prion diseases.

PrP$^{Sc}$ plays a key role in both transmission and pathogenesis of prion diseases (spongiform encephalopathies) and it is a critical factor in neuronal degeneration (Prusiner (1997) The Molecular and Genetic Basis of Neurological Disease, 2nd Edition: 103–143). The most common prion diseases in animals are scrapie of sheep and goats and bovine spongiform encephalopathy (BSE) of cattle (Wilesmith and Wells (1991) Curr Top Microbiol Immunol 172:21–38). Four prion diseases of humans have been identified: (1) kuru, (2) Creutzfeldt-Jakob Disease (CJD), (3) Gerstmann-Straussler-Scheinker Disease (GSS), and (4) fatal familial insomnia (FFI) [Gajdusek (1977) Science 197:943–960; Medori, Tritschler et al. (1992) N Engl J Med 326:444–449]. Initially, the presentation of the inherited human prion diseases posed a conundrum which has since been explained by the cellular genetic origin of PrP.

The assembly and misassembly of normally soluble proteins into conformationally altered proteins is thought to be a causative process in a variety of other diseases. Structural conformational changes are required for the conversion of a normally soluble and functional protein into a defined, insoluble state. Examples of such insoluble protein include: Aβ peptide in amyloid plaques of Alzheimer's disease and cerebral amyloid angiopathy (CAA); α-synuclein deposits in Lewy bodies of Parkinson's disease, tau in neurofibrillary tangles in frontal temporal dementia and Pick's disease; superoxide dismutase in amyotrophic lateral sclerosis; huntingtin in Huntington's disease; and prions in Creutzfeldt-Jakob disease (CJD): (for reviews, see Glenner et al. (1989) J. Neurol. Sci. 94:1–28; Haan et al. (1990) Clin. Neurol. Neurosurg. 92(4):305–310).

Often these highly insoluble proteins form aggregates composed of nonbranching fibrils with the common characteristic of a β-pleated sheet conformation. In the CNS, amyloid can be present in cerebral and meningeal blood vessels (cerebrovascular deposits) and in brain parenchyma (plaques). Neuropathological studies in human and animal models indicate that cells proximal to amyloid deposits are disturbed in their normal functions (Mandybur (1989) Acta Neuropathol. 78:329–331; Kawai et al. (1993) Brain Res. 623:142–6; Martin et al. (1994) Am. J. Pathol. 145:1348–1381; Kalaria et al. (1995) Neuroreport 6:477–80; Masliah et al. (1996) J. Neurosci. 16:5795–5811). Other studies additionally indicate that amyloid fibrils may actually initiate neurodegeneration (Lendon et al. (1997) J. Am. Med. Assoc. 277:825–31; Yankner (1996) Nat. Med. 2:850–2; Selkoe (1996) J. Biol. Chem. 271:18295–8; Hardy (1997) Trends Neurosci. 20:154–9).

In both AD and CAA, the main amyloid component is the amyloid β protein (Aβ). The Aβ peptide, which is generated from the amyloid β precursor protein (APP) by two putative secretases, is present at low levels in the normal CNS and blood. Two major variants, Aβ$_{1-40}$ and Aβ$_{1-42}$, are produced by alternative carboxy-terminal truncation of APP (Selkoe et al.(1988) Proc. Natl. Acad. Sci. USA 85:7341–7345; Selkoe, (1993) Trends Neurosci 16:403–409). Aβ$_{1-42}$ is the more fibrillogenic and more abundant of the two peptides in amyloid deposits of both AD and CAA. In addition to the amyloid deposits in AD cases described above, most AD cases are also associated with amyloid deposition in the vascular walls (Hardy (1997), supra; Haan et al. (1990), supra; Terry et al., supra; Vinters (1987), supra; Itoh et al. (1993), supra; Yamada et al. (1993), supra; Greenberg et al. (1993), supra; Levy et al. (1990), supra). These vascular lesions are the hallmark of CAA, which can exist in the absence of AD.

Human transthyretin (TTR) is a normal plasma protein composed of four identical, predominantly β-sheet structured units, and serves as a transporter of hormone thyroxin. Abnormal self assembly of TTR into amyloid fibrils causes two forms of human diseases, namely senile systemic amyloidosis (SSA) and familial amyloid polyneuropathy (FAP) (Kelly (1996) Curr Opin Strut Biol 6(1):11–7). The cause of amyloid formation in FAP are point mutations in the TTR gene; the cause of SSA is unknown. The clinical diagnosis is established histologically by detecting deposits of amyloid in situ in bioptic material.

To date, little is known about the mechanism of TTR conversion into amyloid in vivo. However, several laboratories have demonstrated that amyloid conversion may be simulated in vitro by partial denaturation of normal human TTR [McCutchen, Colon et al. (1993) Biochemistry 32(45):12119–27; McCutchen and Kelly (1993) Biochem Biophys Res Commun 197(2) 415–21]. The mechanism of conformational transition involves monomeric conformational intermediate which polymerizes into linear β-sheet structured amyloid fibrils [Lai, Colon et al. (1996) Biochemistry 35(20):6470–82]. The process can be mitigated by binding with stabilizing molecules such as thyroxin or triiodophenol (Miroy, Lai et al. (1996) Proc Natl Acad Sci USA 93(26): 15051–6).

The precise mechanisms by which neuritic plaques are formed and the relationship of plaque formation to the disease-associated neurodegenerative processes are not well-defined. The amyloid fibrils in the brains of Alzheimer's and prion disease patients are known to result in the inflammatory activation of certain cells. For example, primary microglial cultures and the THP-1 monocytic cell line are stimulated by fibrillar β-amyloid and prion peptides to activate identical tyrosine kinase-dependent inflammatory signal transduction cascades. The signaling response elicited by β-amyloid and prion fibrils leads to the production of neurotoxic products, which are in part responsible for the neurodegenerative . C. K. Combs et al, J Neurosci 19:928–39 (1999).

Despite efforts to monitor cattle and sheep and prevent importation of animals from countries known for outbreaks of prion diseases there remains a concern about products being contaminated with prions. If food products are contaminated the contamination might not appear in the human population for many years. Thus, the present invention offers a prophylactic approach to a potential enormous contamination problem.

BRIEF DESCRIPTION OF THE DRAWING

FIG. 1 is a schematic drawing of a dendrimer molecule showing the defined "generations" of homodisperse structure created using a repetitive divergent growth technique. The specific diagram is of PAMAM, generation 2.0 (ethylene diamine core).

SUMMARY OF THE INVENTION

The present invention provides compounds and compositions which are mixed with, coated on or added to food products. The invention is particularly directed to food products which are combined with compounds or compositions of the invention in amounts sufficient to provide a prophylactic effect relative to diseases associated with conformationally altered proteins. The compositions of the invention are preferably formulated in a low pH solution. For example, the composition is comprised of acetic acid (vinegar) having dissolved therein branched polycations agents, preferably highly-branched polycations. If the formulation is not low pH then after it is eaten it will enter the low pH environment of the stomach. At that point the polycationic agents will render the conformationally altered protein (e.g., prions) susceptible to proteolytic digestion. Branched polycations for use in the invention include, but are not limited to, polypropylene imine, polyethyleneimine (PEI) poly(4'-aza-4'-methylheptamethylene D-glucaramide), polyamidoamines and suitable fragments and/or variants of these compounds. The compositions can also contain other ingredients, either separate or complexed to the branched polycations. The invention further includes foods (particularly meats) which have the low pH compositions of the invention coated on, mixed with or marinated into the meat. A method of treating food is also described whereby branched polycations are brought into contact with food at a low pH and in sufficient amounts and for a sufficient period of time so as to destroy conformationally altered proteins present in the food. After the proteins are destroyed the pH can be returned to normal.

Compositions of the invention are particularly effective when consumed over a period of time, i.e. food treated via the invention should be consumed over long periods of time—several years.

The invention also features a method of preventing protein deposits in degenerative diseases of a subject by consumption of a food treated with a polycationic compound which is preferably a highly-branched polycation.

An important aspect of the invention is meat and meat products (preferably beef or mutton) with a composition of the invention coated thereon, absorbed into or mixed therewith.

Another aspect of the invention is a food product with meat therein (e.g., soups, broths, extracts, etc.) with polycationic compound coated thereon, absorbed into or mixed therewith.

Another important aspect of the invention is sauces and condiments such as steak sauces, marinades, ketchup, mayonnaise, mustard, etc. at a pH of less than 5 and preferably 4 or less with a composition of the invention mixed therein.

Another embodiment of the invention is a method of spraying or otherwise placing dendrimer compositions on grass, hay or food products eaten by farm animals such as cows or sheep in areas where prion contamination is suspected.

Another embodiment of the invention is fertilizer material mixed with dendrimer compounds.

An advantage of the invention is that compositions of the invention can be added to food products in very low concentrations (e.g., 1 to 500 $\mu$g per ml of composition) and still obtain the desired results.

A feature of the invention is that the compositions (e.g. branched polycationic agents) are non-toxic at very high dosages.

Another aspect of the invention is a method of preventing farm animals from becoming ill by repeatedly treating their food (particularly any meat containing food) with branched polycations at a pH of 4.5 or less.

The invention also features a method for preventing the formation of protein deposits in animals or humans at risk for a degenerative disease by providing for consumption of a highly-branched polycationic compound in an amount sufficient to suppress formation of the protein deposits.

Food products of the invention can be directed to individual genetically predisposed to developing degenerative disease, such as humans genetically at risk for AD, Parkinson's disease, ALS, FTD, Pick's disease, Huntington's disease or CJD. Subjects may also be determined to be at risk due to exposure to infectious agents causing amyloid-associated disorders, e.g. cattle exposed to bovine prions from a BSE contaminated source.

A feature of the compounds of the present invention is their ability to mediate the clearance of $PrP^{Sc}$ from cultured cells under non-cytotoxic conditions.

An advantage of the food additive compositions of the invention is that the highly-branched polycation can be consumed in large amounts because it is non-toxic to the mammalian host at a dosage of 0.001 mg to 1 mg/kg body weight per day.

An important advantage of the invention is that the highly branched polycationic compounds are particularly effective at clearing conformationally altered proteins (e.g. prions) at a low pH which matches the pH of food additives such as vinegar.

These and other objects, advantages, and features of the invention will become apparent to those persons skilled in the art upon reading the details of the compounds, and assay method more fully described below.

DETAILED DESCRIPTION OF PREFERRED EMBODIMENTS

Before the present compositions, food additives and food products are described, it is to be understood that this invention is not limited to the particular compounds, compositions and foods described and, as such, may of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "conformationally altered protein" is used here to describe any protein which has a three dimensional conformation associated with a disease. The conformationally altered protein may cause the disease, be a factor in a symptom of the disease or appear as a result of other factors. The conformationally altered protein appears in another conformation which has the same amino acid sequence. In general, the conformationally altered protein formed is "constricted" in conformation as compared to the other "relaxed" conformation which is not associated with disease. The following is a non-limiting list of diseases with associated proteins which assemble two or more different conformations wherein at least one conformation is an example of a conformationally altered protein.

| Disease | Insoluble Proteins |
|---|---|
| Alzheimer's Disease | APP, Aβ peptide, α1-antichymotrypsin, tau, non-Aβ component, presenillin 1, presenillin 2 apoE |
| Prion diseases, Creutzfeldt Jakob. disease, scrapie and bovine spongiform encephalopathy | PrP$^{Sc}$ |
| ALS | SOD and neurofilament |
| Pick's disease | Pick body |
| Parkinson's disease | α-synuclein in Lewy bodies |
| Frontotemporal dementia | tau in fibrils |
| Diabetes Type 11 | Amylin |
| Multiple myeloma-- plasma cell dyscrasias | IgGL-chain |
| Familial amyloidotic polyneuropathy | Transthyretin |
| Medullary carcinoma of thyroid | Procalcitonin |
| Chronic renal failure | β$_2$--microglobulin |
| Congestive heart failure | Atrial natriuretic factor |
| Senile cardiac and systemic amyloidosis | Transthyretin |
| Chronic inflammation | Serum amyloid A |
| Atherosclerosis | ApoA1 |
| Familial amyloidosis | Gelsolin |
| Huntington's disease | Huntingtin |

The terms "food", "food product" and the like are used interchangeably herein to describe material eaten by an animal to sustain life. Food includes meat (animal flesh used as food) and meat products generally eaten by humans and animal derived protein products eaten by humans, cows and sheep. Food also includes condiments or seasonings generally used by humans on other foods e.g., mustard, ketchup, mayonnaise, and marinades used on beef or mutton. A preferred food product of the invention is in the form of a low pH (3.5±1) liquid such as a steak sauce or marinade which comprises highly branched polycationic compound dissolved, dispersed or mixed therein at a concentration of 1 to 500, preferably 20–60 μg/ml. The term "food" includes animal feed e.g. grass and hay which after being eaten is in the stomach of the animal at a low pH.

The terms "treatment", "treating", "treat" and the like are used herein to generally mean obtaining a desired pharmacologic and/or physiologic effect. The effect obtained by food and food additive compositions of the invention will be prophylactic in terms of completely or partially preventing a disease or symptom thereof. "Treatment" as used herein covers any treatment of a disease in an animal, particularly a human, and includes:

(a) preventing the disease or symptom from occurring in a subject which may be predisposed to the disease or symptom but has not yet been diagnosed as having it;

(b) inhibiting the disease of its symptom, i.e., arresting development of the disease or its symptoms; or (c) relieving the disease symptom, i.e., causing regression of the disease or symptom.

The present invention is directed to the (a) preventing aspect of treating. However, by preventing infection with altered proteins which would be consumed in food the body's natural healing processes alone or in combination with different treatments may also inhibit (b) and relieve (c).

By "effective dose" or "amount effective" is meant an administration of a compound sufficient to provide the desired physiological and/or psychological change. This will vary depending on the individual, the disease and the treatment. The dose should be a prophylactic dose, which should be sufficient to prevent accumulation of insoluble protein deposits to an undesirable level. The dose also relates to the food product. The highly branched polycationic compounds of the invention could be mixed with meat in an amount in a range 1 to 500 μg per ml. The concentration is sufficient if the resulting product is cleared of a sufficient amount of conformationally altered proteins such that consumption of the product over time would not result in infection. Because (1) some foods will have higher concentrations of altered protein than others (2) some foods are eaten more frequently than others and (3) individuals differ in susceptibility to diseases the effective dose or concentration range can vary considerably. It is also pointed out that the dose needed to treat an amount of food may vary somewhat based on the pH the treatment is carried out at and the amount of time the compound is maintained in contact with the food at the desired low pH (e.g., 4.5 or less) level.

The term "$LD_{50}$" as used herein is the dose of an active substance that will result in 50 percent lethality in all treated experimental animals. Although this usually refers to invasive administration, such as oral, parenteral, and the like, it may also apply to toxicity using less invasive methods of administration, such as topical applications of the active substance.

The term "amine-terminated" includes primary, secondary and tertiary amines.

The terms "PrP protein", "PrP" and like are used interchangeably herein and shall mean both the infectious particle form $PrP^{Sc}$ known to cause diseases (spongiform encephalopathies) in humans and animals and the noninfectious form $PrP^{C}$ which, under appropriate conditions is converted to the infectious $PrP^{Sc}$ form.

The terms "prion", "prion protein", "$PrP^{Sc}$ protein" and the like are used interchangeably herein to refer to the infectious $PrP^{Sc}$ form of a PrP protein, and is a contraction of the words "protein" and "infection." Particles are comprised largely, if not exclusively, of $PrP^{Sc}$ molecules encoded by a PrP gene. Prions are distinct from bacteria, viruses and viroids. Known prions infect animals to cause scrapie, a transmissible, degenerative disease of the nervous system of sheep and goats, as well as bovine spongiform encephalopathy (BSE), or "mad cow disease", and feline spongi form encephalopathy of cats. Four prion diseases known to affect humans are (1) kuru, (2) Creutzfeldt-Jakob Disease (CJD), (3) Gerstmann-Sträussler-Scheinker Disease (GSS), and (4) fatal familial insomnia (FFI). As used herein "prion" includes all forms of prions causing all or any of these diseases or others in any animals used-and in particular in humans and domesticated farm animals.

The term "PrP gene" is used herein to describe genetic material which expresses proteins including known polymorphisms and pathogenic mutations. The term "PrP gene" refers generally to any gene of any species which encodes any form of a prion protein. Some commonly known PrP sequences are described in Gabriel et al., *Proc. Natl. Acad. Sci. USA* 89:9097–9101 (1992) and U.S. Pat. No. 5,565,186, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a $PrP^{C}$ (non-disease) or $PrP^{Sc}$ (disease) form.

The terms "standardized prion preparation", "prion preparation", "preparation" and the like are used interchangeably herein to describe a composition (e.g., brain homogenate) obtained from the brain tissue of mammals which exhibits signs of prion disease: the mammal may (1) include a transgene as described herein; (2) have and ablated endogenous prion protein gene; (3) have a high number of prion protein gene from a genetically diverse species; and/or (4) be a hybrid with an ablated endogenous prion protein gene and a prion protein gene from a genetically diverse species. Different combinations of 1–4 are possible, e.g., 1 and 2. The mammals from which standardized prion preparations are obtained exhibit clinical signs of CNS dysfunction as a result of inoculation with prions and/or due to developing the disease of their genetically modified make up, e.g., high copy number of prion protein genes. Standardized prion preparations and methods of making such are described and disclosed in U.S. Pat. No. 5,908,969 issued Jun. 1, 1999 and application serial no. 09/199,523 filed Nov. 25, 1998 both of which are incorporated herein by reference in their entirety to disclose and describe standardized prion preparations.

The term "Alzheimer's disease" (abbreviated herein as "AD") as used herein refers to a condition associated with formation of neuritic plaques comprising amyloid β protein, primarily in the hippocampus and cerebral cortex, as well as impairment in both learning and memory. "AD" as used herein is meant to encompass both AD as well as AD-type pathologies.

The term "AD-type pathology" as used herein refers to a combination of CNS alterations including, but not limited to, formation of neuritic plaques containing amyloid β protein in the hippocampus and cerebral cortex. Such AD-type pathologies can include, but are not necessarily limited to, disorders associated with aberrant expression and/or deposition of APP, overexpression of APP, expression of aberrant APP gene products, and other phenomena associated with AD. Exemplary AD-type pathologies include, but are not necessarily limited to, AD-type pathologies associated with Down's syndrome that is associated with overexpression of APP.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD-associated characteristics.

The term "cerebral amyloid angiopathy" (abbreviated herein as CAA) as used herein refers to a condition associated with formation of amyloid deposition within cerebral vessels which can be complicated by cerebral parenchymal hemorrhage. CAA is also associated with increased risk of stroke as well as development of cerebellar and subarachnoid hemorrhages (Vinters (1987) *Stroke* 18:311–324; Haan et al. (1994) *Dementia* 5:210–213; Itoh et al (1993) *J. Neurol. Sci.* 116:135–414). CAA can also be associated with dementia prior to onset of hemorrhages. The vascular amyloid deposits associated with CAA can exist in the absence of AD, but are more frequently associated with AD.

The term "phenomenon associated with cerebral amyloid angiopathy" as used herein refers to a molecular, structural, or functional event associated with CAA, particularly such an event that is readily assessable in an animal model. Such events include, but are not limited to, amyloid deposition, cerebral parenchymal hemorrhage, and other CAA-associated characteristics.

The term "β-amyloid deposit" as used herein refers to a deposit in the brain composed of Aβ as well as other substances.

Abbreviations used herein include:
CNS for central nervous system;
BSE for bovine spongiform encephalopathy;
CJD for Creutzfeldt-Jakob Disease;
FFI for fatal familial insomnia;
GSS for Gerstmann-Straussler-Scheinker Disease;
AD for Alzheimer's disease;
CAA for cerebral amyloid angiopathy;
Hu for human;
HuPrP for human prion protein;
Mo for mouse;
MoPrP for mouse prion protein;
SHa for a Syrian hamster;
SHaPrP for a Syrian hamster prion protein;
PAMAM for polyamidoamide dendrimers
PEI for polyethyleneimine
PPI for polypropyleneimine
$PrP^{Sc}$ for the scrapie isoform of the prion protein;
$PrP^{C}$ for the cellular contained common, normal isoform of the prion protein;
PrP 27–30 or $PrP^{Sc}$ 27–30 for the treatment or protease resistant form of $PrP^{Sc}$;
$MoPrP^{Sc}$ for the scrapie isoform of the mouse prion protein;
N2a for an established neuroblastoma cell line used in the present studies;
ScN2a for a chronically scrapie-infected neuroblastoma cell line;
ALS for amyotrophic lateral sclerosis;
HD for Huntington's disease;
FTD for frontotemporal dementia;
SOD for superoxide dismutase General Aspects of the Invention The invention comprises compositions of compounds found to be effective in the clearance of conformationally altered proteins. The compositions are preferably low pH solutions comprised of a non-toxic acid such as acetic acid having dissolved therein a branched polycation. Preferred compositions of the invention are in the form of vinegar based marinades or sauces used on beef and/or mutton. The compositions are coated on, mixed with, injected into or otherwise brought into contact with a food, e.g. a meat. The composition is applied in a manner so that the branched polycation is maintained at a low pH (e.g. 5 or less and preferably 3.5±1) in an amount of 1 μg or more polycation per ml of food product. The composition is maintained in the desired pH range at normal temperature (e.g., 15° C. to 30° C.) for a sufficient period of time (e.g. 1 hour to 1 week) to cause conformationally altered protein present on or in the food to be destroyed (e.g. hydrolyzed). After the proteins have been destroyed the pH of the food may be increased to the food's normal pH range or higher.

Dendrimer Compounds which Clear Prions

Dendrimers are branched compounds also known as "starburst" or "star" polymers due to a characteristic star-like structure (see FIG. 1). Dendrimers of the invention are polymers with structures built from $AB_n$ monomers, with $n \geq 2$, and preferably n=2 or 3. Such dendrimers are highly branched and have three distinct structural features: 1) a core, 2) multiple peripheral end-groups, and 3) branching units that link the two. Dendrimers may be cationic (full generation dendrimers) or anionic (half generation dendrimers). For a review on the general synthesis, physical properties, and applications of dendrimers, see, e.g., Tomalia et. al, Angew. *Chem. Int. Ed. Engl.*, 29:138–175, (1990); Y. Kim and C. Zimmerman, *Curr Opin Chem Biol*, 2:733–7421 (1997).

In a preferred embodiment, the food additive compositions of the invention comprise a cationic dendrimer preferably dissolved in a low pH solvent such as vinegar. Examples of suitable dendrimers are disclosed in U.S. Pat. Nos. 4,507,466, 4,558,120, 4,568,737, 4,587,329, 4,631,337, 4,694,064, 4,713,975, 4,737,550, 4,871,779, and 4,857,599 to D. A. Tomalia, et al., which are hereby incorporated by reference to disclose and describe such compounds. Dendrimers typically have tertiary amines which have a pKa of 5.7. The dendrimers can optionally be chemically or heat treated to remove some of the tertiary amines. Other suitable cations include polypropylene imine, polyethyleneimine (PEI), which has tertiary amines with a pKa of 5.9, and poly(4'-aza-4'-methylheptamethylene D-glucaramide), which has tertiary amines with a pKa of 6.0. The cationic dendrimer is preferably dissolved in the low pH solvent such as vinegar in a concentration of 0.0001% or more, preferably 0.01% or more and more preferably about 1%.

Preferably, the dendrimers for use in the invention are polyamidoamines (hereinafter "PAMAM"). PAMAM dendrimers are particularly biocompatible, since polyamidoamine groups resemble peptide bonds of proteins.

Dendrimers are prepared in tiers called generations (see generations 0, 1 and 2 in FIG. 1) and therefore have specific molecular weights. The full generation PAMAM dendrimers have amine terminal groups, and are cationic, whereas the half generation dendrimers are carboxyl terminated. Full generation PAMAM dendrimers are thus preferred for use in the present invention. PAMAM dendrimers may be prepared having different molecular weights and have specific values as described in Table 1 below for generations 0 through 10.

TABLE A

LIST OF PAMAM DENDRIMERS AND THEIR
MOLECULAR WEIGHTS (Ethylene Diamine core, amine terminated).

| GENERATION | TERMINAL GROUPS | MOL. WT. g/mole |
|---|---|---|
| 0 | 4 | 517 |
| 1 | 8 | 1430 |
| 2 | 216 | 3256 |
| 3 | 32 | 6909 |
| 4 | 64 | 14,215 |
| 5 | 128 | 28,795 |
| 6 | 256 | 58,048 |
| 7 | 512 | 116,493 |
| 8 | 1024 | 233,383 |
| 9 | 2048 | 467,162 |
| 10 | 4096 | 934,720 |

As shown in Table A, the number of terminal amine groups for PAMAM dendrimers generations 0 through 10 range from 4 to 4,096, with molecular weights of from 517 to 934,720. PAMAM dendrimers are available commercially from Aldrich or Dendritech. Polyethyleneimine or polypropylene dendrimers or quaternized forms of amine-terminated dendrimers may be prepared as described by Tomalia et. al, Angew, *Chem. Int. Ed. Engl.*, 29:138–175 (1990) incorporated by reference to describe and disclose methods of making dendrimers.

Food Additive Compositions

Examples provided here show that highly-branched polycations, e.g. dendrimer compounds, affect the extent and distribution of $PrP^{Sc}$ protein deposits in scrapie-infected cells. The presence of dendrimers in a low pH environment and at relatively low, non-cytotoxic levels results in a significant reduction in detectable $PrP^{Sc}$ in cells and brain homogenates. Thus, the present invention encompasses food additive compositions for reducing, inhibiting, or otherwise mitigating plaque formation in a subject susceptible to neuronal degenerative disorders associated with protein deposit formation. A composition of the invention is comprised of any compound capable of destroying conformationally altered proteins when in a low pH environment, (e.g. a polycationic dendrimer) in solution, suspension or mixture with a food product.

Formulations

Food additive compositions of the invention preferably contain highly branched polycations, e.g. polycationic dendrimer, in a concentration from 0.0001 to 10% of the formulation. The following methods and excipients are merely exemplary and are in no way limiting.

In addition to including the compound such as a highly branched cationic compound in the formulation it is important to maintain that compound in a low pH environment. Many sauces used with meats include significant amounts of vinegar and other components which would provide the low pH environments. Non-limiting examples of commercially available products which could be supplemented with the cationic compounds are described below. In these formulations the percentage amount of each ingredient can vary. However, the ingredients are generally listed in order with the ingredient listed first present in the largest percentage amount and the last listed ingredient present in the smallest percentage amount. In general the first listed ingredient is present in amounts of 40% to 100% and the last listed ingredient is present in a range of 0.5% to 5%. The other ingredients are present in an amount in a range of 1% to 60% and more generally 5% to 20%. In each case the polycationic compounds of the invention are added in amounts of about 0.01% to 5% and preferably 0.1% to 2% and more preferably about 1%. The amount added is an amount needed to obtain the desired effect.

| | H.J. Heinz Co. Tomato Ketchup | | Heaven and Earth Raspberry Hoisin Sauce |
|---|---|---|---|
| Ingredients: | tomato concentrate made from red ripe tomatoes | Ingredients: | raspberry puree |
| | distilled vinegar | | Hoisin Sauce (sugar, vinegar, soya bean, water, salt, wheat flour, garlic, sesame seed, chili spices, artificial color FD + C red #40) |
| | high fructose corn syrup | | sugar |
| | corn syrup | | balsamic vinegar |
| | salt | | sesame seed oil |
| | onion powder | | lime juice |
| | spice | | kosher salt |
| | natural flavoring | | |

-continued

| | Herdez Corporation<br>El Torito<br>Serrano Ranch Dressing | | Herdez Corporation<br>El Torito<br>Cilantro Pepita Caesar Dressing |
|---|---|---|---|
| Ingredients: | soybean oil<br>buttermilk<br>water<br>tomatoes<br>distilled vinegar<br>egg yolk<br>high fructose corn syrup<br>salt<br>serrano peppers<br>onion (dehydrated)<br>spices<br>garlic (dehydrated)<br>potassium sorbate and sodium benzoate added as preservatives<br>natural flavor<br>xanthan gum<br>artificial color<br>lactic acid<br>polysorbate 60<br>lime juice concentrate<br>calcium chloride<br>calcium disodium EDTA added to protect flavor | Ingredients: | soybean oil<br>water<br>red wine vinegar<br>green chilies<br>cotija cheese (milk, nonfat milk, cheese cuiture, enzymes)<br>egg yolk<br>cilantro<br>high fructose corn syrup<br>pumpkin seeds (pepitas)<br>garlic<br>salt<br>parmesan cheese (part-skim milk, cheese cultures, salt, enzymes)<br>lactic acid<br>potassium sorbate and sodium benzoate added as preservatives<br>spice<br>xanthan gum<br>carmel color<br>propylene glycol alginate<br>natural flavors<br>yellow #5<br>calcium disodium EDTA added to protect flavor<br>blue #1 |

| | Nabisco<br>A.1. Steak Sauce | | Marin Gourmet<br>Fresh Blueberry Fruity & Tangy<br>Salad Dressing & Marinade |
|---|---|---|---|
| Ingredients: | tomato puree (water, tomato paste)<br>distilled vinegar<br>corn syrup<br>salt<br>raisin paste<br>spices and herbs<br>crushed orange puree<br>dried garlic and onion<br>caramel color<br>potassium sorbate<br>xanthan gum | Ingredients: | fresh blueberry<br>balsamic & aged wine<br>blueberry vinegar<br>italian olive oil<br>honey and dijon mustard<br>orgainc herbs<br>peppercorn<br>capers<br>spices<br>sea salt |

| | Wild Thymes<br>Orange Citrus Vinaigrette | | Grapevine Trading Co., Inc.<br>California Harvest Pear Vinegar |
|---|---|---|---|
| Ingredients: | champagne vinegar<br>canola/olive oil<br>orange concentrate<br>honey<br>lemon juice<br>sweet red peppers<br>carrots<br>scallions<br>garlic<br>onions<br>herbs<br>spices<br>sea salt | Ingredients: | California champagne vinegar (50 grain, contains sulfites)<br>California pear essence |

| | Whole Foods Market<br>Organic Yellow Mustard | | Christie Food Products Inc.<br>Firehouse No. 2 Bar-B-Aue Sauce<br>(Hot & Spicey) |
|---|---|---|---|
| Ingredients: | organic apple cider vinegar<br>organic rnustard seed<br>salt<br>tumeric<br>spices | Ingredients: | tomato puree<br>brown sugar<br>corn syrup<br>distilled white vinegar<br>red wine vinegar<br>soybean oil<br>soy sauce (water, soybeans, salt, alcohol)<br>spices<br>modified food starch<br>salt |

-continued

|  |  |  | natural flavors<br>Worcestershire sauce (see below)<br>onion powder<br>garlic powder<br>crushed red pepper<br>cayenne pepper |
|---|---|---|---|
|  | Whole Foods Market<br>Barbeque Sauce<br>(tangy) |  | Lea & Perrins, Inc.<br>Worcestershire Sauce |
| Ingredients: | tomato puree (tomatoes and water<br>apple cider vinegar<br>tamari sauce (water, organic<br>soybeans, organic whole<br>wheat and salt<br>honey<br>mustard (vinegar, water, mustard<br>seed, salt, turmeric, spices)<br>lemon juice<br>spices<br>sea salt<br>red bell pepper<br>pepper sauce (vinegar, red pepper,<br>salt)<br>natural hickory smoke<br>molasses<br>natural vegetable gum<br>mustard flour<br>lemon peel | Ingredients: | vinegar<br>molasses<br>high fructose corn syrup<br>anchovies<br>water<br>hydrolized soy and corn protein<br>onions<br>tamarinds<br>salt<br>garlic<br>cloves<br>chili peppers<br>natural flavorings<br>shallots |
|  | Yamasa Corporation<br>Soy Sauce<br>(Less Salt 45) |  |  |
| Ingredients: | water<br>soybeans<br>wheat<br>sea salt<br>vinegar<br>alcohol (to preserve freshness)<br>lactic acid |  |  |

Compositions of mayonnaise and dressings described in U.S. Pat. No. 5,683,737 could be combined with any polycation described here as could compositions comprising apricot vinegar taught in U.S. Pat. No. 5,882,709. Further, these and other compositions could be combined with those taught in U.S. Pat. No. 4,777,052—see also 4,869,915.

The above listed food formulations are all liquids and are for human consumption. However, the branched polycations can be coated onto, injected into or otherwise brought into contact with a solid or semi-solid food thereby creating other formulations of the invention. Further, the branched polycations can be combined with animal feed—particularly animal feed containing meat or meat by products of other animals. Low pH solutions of polycations can be sprayed on grass, hay or other feed for animals such as cattle believed to be a high risk for prion diseases, e.g. "mad cow" disease.

Compounds such as dendrimers may be formulated with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for use in pourable foods by dissolving, suspending or emulsifying them in an aqueous or nonaqueous solvent, such as vinegar, vegetable or other similar oils, synthetic aliphatic acid glycerides, esters of higher aliphatic acids or propylene glycol. The formulations may also contain conventional additives such as solubilizers, isotonic agents, suspending agents, emulsifying agents, stabilizers and preservatives. Preferred additives lower the pH of the compositions, e.g., vinegars and various pepper extracts.

The formulations of the invention have the advantage that they are non-toxic in tested forms of administration. For example, parenteral administration of a solution of the formulations of the invention is preferably nontoxic at a dosage of 0.1 mg/mouse, which is an $LD_{50}$ of less than one at 40 mg/Kg. Various injectable formulations of the type known to those skilled in the art can be used to delivery compounds of the invention.

Those skilled in the art will understand that in some situations it may be desirable to further reduce the pH environment to obtain the desired results. This can be accomplished by adding any desired acid. If desired, the pH can be raised to a normal level for that food product after treatment is complete, i.e. after a sufficient amount of any conformationally altered protein present are destroyed.

Compounds effective in destroying conformationally altered proteins are determined via a cell culture assay and an organ homogenate assay each of which is described below in detail.

ScN2a Cell Based Assay

Efforts were made to optimize the transfection of ScN2a cells with pSPOX expression plasmids (Scott, M. R., Kohler, R., Foster, D. & Prusiner, S. B. Chimeric prion protein expression in cultured cells and transgenic mice.

Protein Sci. 1, 986–997 (1992)). In connection with those effects an evaluation was made of a transfection protocol that used SuperFect reagent (QIAGEN®). It was found that epitope-tagged (MHM2) PrP$^{Sc}$ (Scott, M. R., Köhler, R., Foster, D. & Prusiner, S. B. Chimeric prion protein expression in cultured cells and transgenic mice. Protein Sci. 1, 986–997 (1992)) could not be detected in ScN2a cells following SuperFect-mediated transfection, whereas MHM2 PrP$^{Sc}$ was efficiently formed when a cationic liposome method for DNA delivery was used. Close scrutiny revealed that, prior to protease digestion, SuperFect-transfected samples expressed MHM2 bands, which are not seen in the background pattern of an untransfected sample. The 3F4 monoclonal antibody does not react with MoPrP but does exhibit high background staining on Western blots of mouse ScN2a cells. Increased immunostaining in the 20–30 kDa region was observed compared to the non-transfected sample. These observations led us to conclude that MHM2 PrP was successfully expressed using SuperFect transfection reagent, but that conversion of MHM2 PrP$^C$ to protease-resistant MHM2 PrP$^{Sc}$ was inhibited by SuperFect.

To investigate this apparent inhibition, a Western blot was reprobed with RO73 polyclonal antiserum to detect endogenous MoPrP$^{Sc}$, the presence of which is diagnostic for prion infection in ScN2a cells (Butler, D. A., et al. Scrapie-infected murine neuroblastoma cells produce protease-resistant prion proteins. J. Virol. 62, 1558–1564 (1988)). Surprisingly, it was found that the SuperFect-treated ScN2a cells no longer contained detectable quantities of MoPrP$^{Sc}$ - also confirmed in Western blots. To investigate the mechanism by which SuperFect reduced the level of pre-existing PrP$^{Sc}$ in chronically infected ScN2a cells, measurements were made of endogenous PrP$^{Sc}$ in ScN2a cells exposed to various concentrations of SuperFect in the absence of plasmid DNA. The results showed that treatment with SuperFect (a branched polycation) caused the disappearance of PrP$^{Sc}$ from ScN2a cells in a dose-dependent manner. The concentration of SuperFect required to eliminate >95% of pre-existing PrP$^{Sc}$ with a three hour exposure was found to be about 150 μg/ml. Duration of treatment also influenced the ability of SuperFect to remove PrP$^{Sc}$ from ScN2a cells: exposure to 150 μg/ml SuperFect for 10 min did not affect PrP$^{Sc}$ levels, whereas 7.5 μg/ml SuperFect eliminated all detectable PrP$^{Sc}$ with a t½=8 h.

SuperFect is a mixture of branched polyamines derived from heat-induced degradation of a PAMAM dendrimer (Tang, M. X., Redemann, C. T. & Szoka, F. C. J. In vitro gene delivery by degraded polyamidoamine dendrimers. Bioconjug. Chem. 7, 703–714 (1996)). Knowing this structure the ability of several other branched and unbranched polymers to eliminate PrP$^{Sc}$ from ScN2a cells (Table 1). The branched polymers investigated include various preparations of PEI, as well as intact PAMAM and PPI dendrimers. Dendrimers are manufactured by a repetitive divergent growth technique, allowing the synthesis of successive, well-defined "generations" of homodisperse structures (FIG. 1). The potency of both PAMAM and PPI dendrimers in eliminating PrP$^{Sc}$ from ScN2a cells increased as the generation level increased. The most potent compounds with respect to eliminating PrP$^{Sc}$ were PAMAM generation 4.0 and PPI generation 4.0, whereas PAMAM generation 1.0 showed very little ability to eliminate PrP$^{Sc}$ (Table 1). Similarly, a high MW fraction of PEI was more potent than low MW PEI.

From the foregoing data, it is clear that for all three branched polyamines tested, increasing molecular size corresponded to an increased potency for eliminating PrP$^{Sc}$. To determine whether this trend was directly attributable to increased surface density of amino groups on the larger molecules, PAMAM-OH generation 4.0 was tested. This is a dendrimer that resembles PAMAM generation 4.0 except that hydroxyls replace amino groups on its surface. Unlike PAMAM generation 4.0, PAMAM-OH generation 4.0 did not cause a reduction of PrP$^{Sc}$ levels even at the highest concentration tested (10 mg/ml), establishing that the amino groups are required for the elimination of PrP$^{Sc}$ by PAMAM (Table 1).

In an effort to assess the contribution of the branched architecture to the clearing ability of polyamines for PrP$^{Sc}$, the linear molecules poly-(L)lysine and linear PEI were also tested. Both of these linear compounds were less potent than a preparation of branched PEI with similar average molecular weight (Table 1), establishing that a branched molecular architecture optimizes the ability of polyamines to eliminate PrP$^{Sc}$, presumably because the branched structures achieve a higher density of surface amino groups.

Kinetics of PrP$^{Sc}$ elimination by polyamines.

The preceding results demonstrate the potent ability of branched polyamines to clear PrP$^{Sc}$ from ScN2a cells within a few hours of treatment. The utility of these compounds to act as therapeutics for treatment of prion disease was tested by determining whether they were cytotoxic for ScN2a cells, using as criteria cell growth, morphology, and viability as measured by trypan blue staining. None of the compounds was cytotoxic to ScN2a cells after exposure for one week at concentrations up to 7.5 μg/ml. To determine whether branched polyamines can cure ScN2a cells of scrapie infection without affecting cell viability, the kinetics of prion clearance was examined in the presence of a non-cytotoxic concentration (7.5 μg/ml) of three different branched polyamines. ScN2a cells were exposed to SuperFect, PEI, or PAMAM generation 4.0 for varying periods of time. The kinetics of PrP$^{Sc}$ elimination were assessed by Western blotting. All three compounds caused a substantial reduction in PrP$^{Sc}$ levels after 8–16 h of treatment, and of the three compounds, PEI appeared to remove PrP$^{Sc}$ most quickly, with a t½=4h.

Curing neuroblastoma cells of scrapie infection.

The above results show that it is possible to reverse the accumulation of PrP$^{Sc}$ in ScN2a cells under non-cytotoxic conditions. It was also found that extended exposure to even lower levels of the branched polyamines (1.5 μg/ml) was sufficient to eliminate PrP$^{Sc}$. Based on these findings, this protocol was used to determine whether the severe reduction in PrP$^{Sc}$ levels following exposure to branched polyamines would persist after removal of the compounds. Following the exposure of ScN2a cells to a 1.5 μg/ml SuperFect for 1 week, PrP$^{Sc}$ was reduced to <1% of the baseline level, but then increased back to ~5% of the baseline level after 3 additional weeks in culture in the absence of polyamine. In contrast, following exposure to 1.5 μg/ml of either PEI or PAMAM generation 4.0 for 1 week, PrP$^{Sc}$ was completely eliminated and did not return even after 3 weeks in culture without polyamines. A more intensive course of treatment with 1.8 μg/ml SuperFect for 9 d also cured ScN2a cells of scrapie infection fully, manifested by the absence of PrP$^{Sc}$ 1 month after removal of SuperFect.

Evidence for polyamines acting within an acidic compartment.

The above results showed the potent activity of branched polyamines in rapidly clearing scrapie prions from cultured ScN2a cells. Based on these results the mechanism by which these compounds act was investigated. All of the compounds which effect removal of PrP$^{Sc}$ from ScN2a cells are known to traffic through endosomes (Boussif, O., et al. A versatile vector for gene and oligonucleotide transfer into cells in culture and in vivo: polyethyleneimine. Proc. Natl. Acad. Sci. U.S.A. 92, 7297–7301 (1995); Haensler, J. & Szoka, F. C. J. Polyamidoamine cascade polymers mediate efficient transfection of cells in culture. *Bioconjug. Chem.* 4, 372–379 (1993)). Since $PrP^C$ is converted into $PrP^{Sc}$ in caveolae-like domains (CLDs) or rafts (Gorodinsky, A. & Harris, D. A. Glycolipid-anchored proteins in neuroblastoma cells form detergent-resistant complexes without caveolin. *J Cell Biol.* 129, 619–627 (1995); Taraboulos, A., et al. Cholesterol depletion and modification of COOH-terminal targeting sequence of the prion protein inhibits formation of the scrapie isoform. *J Cell Biol.* 129, 121–132 (1995); Vey, M., et al. Subcellular colocalization of the cellular and scrapie prion proteins in caveolae-like membranous domains. *Proc. Natl. Acad. Sci. USA* 93, 14945–14949 (1996); Kaneko, K., et al. COOH-terminal sequence of the cellular prion protein directs subcellular trafficking and controls conversion into the scrapie isoform. *Proc. Natl Acad. Sci. USA* 94, 2333–2338 (1997)) and is then internalized through the endocytic pathway (Caughey, B., Raymond, G. J., Ernst, D. & Race, R. E. N-terminal truncation of the scrapie-associated form of PrP by lysosomal protease(s): implications regarding the site of conversion of PrP to the protease-resistant state. *J. Virol.* 65, 6597–6603 (1991); Borchelt, D. R., Taraboulos, A. & Prusiner, S. B. Evidence for synthesis of scrapie prion proteins in the endocytic pathway. *J Biol. Chem.* 267, 16188–16199 (1992)), it was deduced that polyamines act upon $PrP^{Sc}$ in endosomes or lysosomes. This deduction was investigated by determining the effect of pretreatment with the lysosomotropic agents chloroquine and $NH_4Cl$ on the ability of polyamines to eliminate PrPSc. These lysosomotropic agents alkalinize endosomes and have no effect on $PrP^{Sc}$ levels when administered to ScN2a cells (Taraboulos, A., Raeber, A. J., Borchelt, D. R., Serban, D. & Prusiner, S. B. Synthesis and trafficking of prion proteins in cultured cells. *Mol. Biol. Cell* 3, 851–863 (1992)). Experimental results obtained shows that 100 μM chloroquine, but not 30 μM $NH_4Cl$, blocked the ability of PEI to eliminate $PrP^{Sc}$. Similar results were obtained with SuperFect and PAMAM, generation 4.0. Although the failure of $NH_4Cl$ to affect $PrP^{Sc}$ levels is not easily explained, the ability of chloroquine to attenuate the ability of branched polyamines to remove $PrP^{Sc}$ is consistent with the notion that these agents act in endosomes or lysosomes.

Organ Homogenate Assay

The above results with cell cultures prompted investigating the possibility that in an acidic environment branched polyamines, either by indirectly interacting with $PrP^{Sc}$ or with another cellular component, could cause $PrP^{Sc}$ to become susceptible to hydrolases present in the endosome/lysozome. An in vitro degradation assay was developed to evaluate the effect of pH on the ability of polyamines to render $PrP^{Sc}$ sensitive to protease. Crude homogenates of scrapie-infected mouse brain were exposed to a broad range of pH values in the presence or absence of SuperFect and then treated with proteinase K prior to Western blotting. Whereas $PrP^{Sc}$ remained resistant to protease hydrolysis throughout the pH range (3.6–9.6) in the absence of Superfect, addition of the branched polyamine at pH 4.0 or below caused $PrP^{Sc}$ to become almost completely degraded by protease.

Polyamine addition showed a dramatic effect on clearance in vitro which was optimized at pH 4 or less. These results show that polyamines act on $PrP^{Sc}$ in an acidic compartment. To establish that the in vitro degradation assay is a valid approximation of the mechanism by which branched polyamines enhance the clearance of $PrP^{Sc}$ from cultured cells, a structure activity analysis was performed with several of the compounds tested in culture cells. An excellent correlation was found between the clearance of $PrP^{Sc}$ in cultured ScN2a cells (Table 1) and the ability to render $PrP^{Sc}$ susceptible to protease at acidic pH in vitro. Notably, PAMAM-OH generation 4.0 failed to render $PrP^{Sc}$ susceptible to protease, whereas PAMAM generation 4.0 and PPI, generation 4.0 exhibited an even stronger activity than Superfect in vitro, as expected from their observed potency in cultured ScN2a cells (Table 1).

Mechanism of Action

The results discussed here show that certain branched polyamines cause the rapid elimination of $PrP^{Sc}$ from ScN2a cells in a dose- and time-dependent manner. These compounds demonstrate a potent ability to remove prions from cultured cells at concentrations that are completely non-cytotoxic. The cells may be maintained indefinitely in culture in the presence of therapeutic levels of branched polyamines. Furthermore, when ScN2a cells were exposed to these compounds for ~1 week, $PrP^{Sc}$ was reduced to undetectable levels and remained so for at least one month after removal of the polyamine.

Clarification of the exact mechanism of $PrP^{Sc}$ elimination by branched polyamines is an important objective. Although a number of possible scenarios exist, several possibilities may be excluded already. One possibility that was eliminated was that polyamines act by induction of chaperones such as heat shock proteins that mediate prion protein refolding because the above results show that it was possible to reproduce the phenomenon in vitro. Furthermore polyamines seem to offer advantages over other putative therapeutics that would seek to promote refolding: at very high concentrations, dimethyl sulfoxide (DMSO) and glycerol act as direct "chemical chaperones" and inhibit the formation of new $PrP^{Sc}$ (Tatzelt, J., Prusiner, S. B. & Welch, W. J. Chemical chaperones interfere with the formation of scrapie prion protein. *EMBO J.* 15, 6363–6373 (1996)), but these compounds cannot reduce pre-existing $PrP^{Sc}$ levels. Furthermore, polyamines inhibit $PrP^{Sc}$ formation at much lower concentrations than these agents. The ability of polyamines to effect the rapid clearance of $PrP^{Sc}$ also contrasts with the activity of other potential prion therapeutics. Sulfated polyanions may inhibit $PrP^{Sc}$ accumulation in ScN2a cells by directly binding to $PrP^C$ (Gabizon, R., Meiner, Z., Halimi, M. & Ben-Sasson, S. A. Heparin-like molecules bind differentially to prion-proteins and change their intracellular metabolic fate. *J Cell. Physiol.* 157, (1993); Caughey, B., Brown, K., Raymond, G. J., Katzenstein, G. E. & Thresher, W. Binding of the protease-sensitive form of PrP (prion protein) to sulfated glycosaminoglycan and Congo red. *J. Virol.* 68, 2135–2141 (1994)), but because branched polyamines are able to clear pre-existing $PrP^{Sc}$, their mechanism of action cannot simply involve binding to $PrP^C$ and inhibiting de novo synthesis.

Another possible mechanism which can be excluded is endosomal rupture. The branched polyamines which were effective in clearing $PrP^{Sc}$ from ScN2a cells in our experiments, PEI, SuperFect and PAMAM, are also potent lysosomotropic, osmotic agents which can swell in acidic environments and rupture endosomes (Boussif, O., et al. A versatile vector for gene and oligonucleotide transfer into cells in culture and in vivo: polyethyleneimine. *Proc. NatL. Acad. Sci. U.S.A.* 92, 7297–7301 (1995); Haensler, J. & Szoka, F. C. J. Polyamidoamine cascade polymers mediate efficient transfection of cells in culture. *Bioconjug. Chem.* 4, 372–379 (1993)). This might suggest that branched polyamines clear $PrP^{Sc}$ from ScN2a cells by rupturing endosomes and exposing $PrP^{Sc}$ to cytosolic degradation processes. However, it is known that the lysosomotropic, endosome-rupturing agents $NH_4Cl$, chloroquine, and monensin do not interfere with the formation of $PrP^{Sc}$ in ScN2a cells (Taraboulos, A., Raeber, A. J., Borchelt, D. R., Serban, D. & Prusiner, S. B. Synthesis and trafficking of prion proteins in cultured cells. *Mol. Biol. Cell* 3, 851–863

(1992)). Furthermore, the results also show that chloroquine interferes with the ability of branched polyamines to clear $PrP^{Sc}$ and that polyamines can clear $PrP^{Sc}$ in vitro at acidic pH in the absence of cell membranes. Together, these observations rule out endosome rupture as the mechanism by which branched polyamines remove $PrP^{Sc}$.

Without committing to any particular mechanism of action it appears likely that branched polyamines require the acidic environment of intact endosomes or lyzosomes to destroy $PrP^{Sc}$. The structure-activity profile of polymers tested reveals that the most active compounds possess densely packed, regularly-spaced amino groups, suggesting that these compounds may bind to a ligand which has periodically-spaced negative charges. Several scenarios remain possible. (1) Branched polyamines may bind directly to $PrP^{Sc}$ arranged as an amyloid with exposed negatively-charged moieties and induce a conformational change under acidic conditions. (2) Treatment of PrP 27–30 with acid decreases turbidity and increases a-helical content, suggesting that such conditions might dissociate $PrP^{Sc}$ into monomers (Safar, J., Roller, P. P., Gajdusek, D. C. & Gibbs, C. J., Jr. Scrapie amyloid (prion) protein has the conformational characteristics of an aggregated molten globule folding intermediate). It is therefore possible that polyamines bind to an equilibrium unfolding intermediate of $PrP^{Sc}$ present under acidic conditions. (3) Alternatively, polyamines might sequester a cryptic, negatively charged component bound to $PrP^{Sc}$ that is essential for protease resistance, but which is only released when $PrP^{Sc}$ undergoes an acid-induced conformational change. Such a component might act as a chaperone for $PrP^{Sc}$ inside endosomes or lysosomes. (4) Finally, another possibility is that polyamines activate an endosomal or lysosomal factor which can induce a conformational change in $PrP^{Sc}$. Clearly, more work will be required to determine the precise mechanism by which branched polyamines destroy $PrP^{Sc}$.

General Applicability of Assay

The in vitro assay described here is generally applicable in the search for compounds that effectively clear conformationally altered proteins present in food thereby preventing a number of degenerative diseases, where the accumulation of proteins seems to mediate the pathogenesis of these illnesses. By simulating lysosomes, where proteases hydrolyze proteins under acidic conditions, the in vitro brain homogenate assay is able to rapidly evaluate the efficacy of a variety of polyamines to induce degradation of $PrP^{Sc}$.

The in vitro assay which used scrapie infected brain homogenate to test for compounds which clear $PrP^{Sc}$ could be modified to assay for compounds which would clear any conformationally altered protein. The assay is carried out by homogenizing the organ or tissue where the conformationally altered protein is present in the highest concentration. The pH of the homogenate is then reduced to less than 5.0 and preferably 4.0 or less. For example pancreatic tissue can be homogenized to produce an assay to test for compounds which clear amylin which is associated with type II Diabetes. Homogenized kidney could be used to test for compounds which clear $\beta_2$ - microglobulin and homogenized heart or vascular tissue used to test for compounds which clear atrial natriuretic factor. Those skilled in the art will recognize other organs and tissue types which can be homogenized to test for other compounds which clear other conformnationally altered proteins.

Besides using the in vitro assay to screen for potential drugs, the compounds found via the assay such as branched polyamines provide a new tool for exploring the conversion of a protein to conformationally altered protein, e.g. $PrP^{C}$ into $PrP^{Sc}$. The mechanism by which branched polyamines render $PrP^{Sc}$ susceptible to proteolysis, remains to be established. Whether the interaction of branched polyamines with $PrP^{Sc}$ is reversible is unknown. In addition, we do not know whether branched polyamines are able to solubilize $PrP^{Sc}$ without irreversibly denaturing the protein. Whatever the mechanism by which branched polyamines interact with $PrP^{Sc}$, it is likely to be different from that found with chaotropes as well as denaturing detergents and solvents (Prusiner, S. B., Groth, D., Serban, A., Stahl, N. & Gabizon, R. Attempts to restore scrapie prion infectivity after exposure to protein denaturants. *Proc. Natl. Acad. Sci. USA* 90, 2793–2797 (1993)).

Using the assays described and disclosed here certain specific branched polyamines have been found which mediate the clearance of $PrP^{Sc}$ from cultured cells under non-cytotoxic conditions. These compounds offer the intriguing possibility of being added to a wide range of low pH food products to neutralize conformational altered proteins present. Since the compounds found act by stimulating normal cellular pathways of protein degradation to destroy $PrP^{Sc}$, this class of compounds would also likely be of value in the treatment of other degenerative and hereditary disorders where abnormally folded, wild-type or mutant proteins accumulate. Such an approach may find merit in developing an effective therapeutics for one or more of the common, degenerative illnesses including Alzheimer's disease, Parkinson's disease, amyotrophic lateral sclerosis, frontotemporal dementia, adult onset diabetes mellitus and the amyloidoses (Beyreuther, K. & Masters, C. L. Serpents on the road to dementia and death. Accumulating evidence from several studies points to the normal function of presenilin 1 and suggests how the mutant protein contributes to deposition of amyloid plaques in Alzheimer's disease. *Nature Medicine* 3, 723–725 (1997); Masters, C. L. & Beyreuther, K. Alzheimer's disease. BMJ316, 446–448 (1998); Selkoe, D. J. The cell biology of beta-amyloid precursor protein and presenilin in Alzheimer's disease. Trends in *Cell Biol.* 8, 447–453 (1998); Selkoe, D. J. Translating cell biology into therapeutic advances in Alzheimer's disease. *Nature* 399, A23–31 (1999); Wong, P. C., et al. An adverse property of a familial ALS-linked SOD1 mutation causes motor neuron disease characterized by vacuolar degeneration of mitochondria. *Neuron* 14, 1105–1116 (1995); Spillantini, M. G., Crowther, R. A., Jakes, R., Hasegawa, M. & Goedert, M. a-Synuclein in filamentous inclusions of Lewy bodies from Parkinson's disease and dementia with Lewy bodies. *Proc. Natl. Acad. Sci. USA* 95, 6469–6473 (1998); Hutton, M., et al. Association of missense and 5'-splice-site mutations in tau with the inherited dementia FTDP-17. *Nature* 393, 702–705 (1998); Stone, M. J. Amyloidosis: a final common pathway for protein deposition in tissues. *Blood* 75, 531–545 (1990)). Whether branched polyamines might also prove efficacious in a variety of inherited disorders where the accumulation of abnormal proteins is a hallmark of the illness remains to be established; these genetic maladies include heritable forms of prion disease, Alzheimer's disease, Parkinson's disease, amyotrophic lateral sclerosis, frontotemporal dementia, Pick's disease and amyloidosis, as well as the triplet repeat diseases including Huntington's disease, spinal cerebellar ataxias and myotonic dystrophy (Fu, Y.-H., et al. An unstable triplet repeat in a gene related to myotonic muscular dystrophy. *Science* 255, 1256–1259 (1992); Group, T.H.s.D.C.R. A novel gene containing a trinucleotide repeat that is expanded and unstable on Huntington's disease chromosomes. *Cell* 72, 971–983 (1993)). Compounds identified via assays of the invention such as branched polyamines will find utility in preventing or delaying the onset of these genetic diseases where carriers can often be identified decades in advance of detectable neurologic or systemic dysfunction.

The invention is based on the discovery that several dendritic polycations, including the starburst dendrimers Superfect™ (QIAGEN®, Valencia, Calif.), polyamidoamide (PAMAM), and the hyperbranched polycation polyethyleneimine (PEI), were surprisingly found to eliminate PrP$^{Sc}$ from cultured scrapie-infected neuroblastoma cells. These highly-branched, polycationic compounds provide a novel class of therapeutic agents to combat prion diseases and other degenerative disease including the amyloidoses. The removal of $PrP^{Sc}$ is dependent on both the concentration of dendritic polymer and length of exposure. Dendritic polymers were able to clear $PrP^{Sc}$ at concentrations which were not cytotoxic. Repeated exposures to heat-degraded starburst PAMAM dendrimer or PEI caused a dramatic reduction in $PrP^{Sc}$ levels which persisted for a month even after removal of the compound. Dendritic polycations did not appear to destroy purified $PrP^{Sc}$ in vitro, and therefore may act through a generalized mechanism. Dendritic polycations represent a class of compounds which can be used as therapeutic agents in prion diseases and other disorders involving insoluble protein deposits, such as the amyloidoses.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

Chemicals. High molecular weight PEI was purchased from Fluka. DOTAP cationic lipid was purchased from Boehringer Mannheim and SuperFect transfection reagent was purchased from QIAGEN®. All other compounds were purchased from Sigma-Aldrich. All test compounds were dissolved in water at stock concentration of 3 mg/ml and filtered through a Millipore 0.22 mm filter.

Cultured cells. Stock cultures of ScN2a cells were maintained in MEM with 10% FBS, 10% Glutamax (Gibco BRL), 100 U penicillin, and 100 mg/ml streptomycin (supplemented DME). Immediately prior to addition of test compounds, the dishes were washed twice with fresh supplemented DME media. After exposure to test compounds, dishes were drained of media and cells were harvested by lysis in 0.25–1 ml 20 mM Tris pH 8.0 containing 100 mM NaCl, 0.5% NP-40, and 0.5% sodium deoxycholate to obtain a total protein concentration of 1 mg/ml measured by the BCA assay. Nuclei were removed from the lysate by centrifugation at 2000 rpm for 5 min. For samples not treated with proteinase K, 40 μl of whole lysate (representing 40 μg total protein) was mixed with an equal volume of 2×SDS reducing sample buffer. For proteinase K digestion, 20 μg/ml proteinase K (Boehringer Mannheim) (total protein:enzyme ratio =50:1) was added, and the sample was incubated for 1 h at 37° C. Proteolytic digestion was terminated by the addition of Pefabloc to a final concentration of 5 mM. One ml samples were centrifuged at 100,000×g for 1 h at 4° C., the supernatants were discarded, and the pellets were resuspended in 80 μl of reducing SDS sample buffer for SDS-PAGE.

Brain homogenates. Brain homogenates from RML scrapie-affected CD-1 mice (10% (w/v) in sterile water) were prepared by repeated extrusion through syringe needles of successively smaller size, from 18 to 22 gauge. Nuclei and debris were removed by centrifugation at 1000 ×g for 5 min. The bicinchnoninic acid (BCA) protein assay (Pierce) was used to determine protein concentration. Homogenates were adjusted to 1 mg/ml protein in 1% NP-40. For reactions, 0.5 ml homogenate was incubated with 25 ml 1.0 M buffer (sodium acetate for pH 3–6 and Tris acetate for pH 7–10) plus or minus 10 ml of polyamine stock solution (3 mg/ml) for 2 h at 37° C. with constant shaking. The final pH value of each sample was measured directly with a calibrated pH electrode (Radiometer Copenhagen). Following incubation, each sample was neutralized with an equal volume 0.2 M HEPES pH 7.5 containing 0.3 M NaCl and 4% Sarkosyl. Proteinase K was added to achieve a final concentration of 20 μg/ml, and samples were incubated for 1 h at 37° C. Proteolytic digestion was terminated by the addition of Pefabloc to a final concentration of 5 μM. Ten μl of digested brain homogenate was mixed with equal volume 2×SDS sample buffer and analyzed by SDS-PAGE followed by Western blotting.

Western blotting. Following electrophoresis, Western blotting was performed as previously described (Scott, M., et al. Transgenic mice expressing hamster prion protein produce species-specific scrapie infectivity and amyloid plaques. *Cell* 59, 847–857 (1989)). Samples were boiled for 5 min and cleared by centrifugation for 1 min at 14,000 rpm in aBeckman ultrafuge. SDS-PAGE was carried out in 1.5 mm, 12% polyacrylamide gels(Laemmli, U. K. Cleavage of structural proteins during the assembly of the head of bacteriophage T-4. *Nature* 227, 680–685 (1970)). Membranes were blocked with 5% non-fat milk protein in PBST (calcium- and magnesium-free PBS plus 0.1% Tween 20) for 1 h at room temperature. Blocked membranes were incubated with primary RO73 polyclonal antibody (to detect MoPrP) (Serban, D., Taraboulos, A., DeArmond, S. J. & Prusiner, S. B. Rapid detection of Creutzfeldt-Jakob disease and scrapie prion proteins. *Neurology* 40, 110–117 (1990)) or 3F4 monoclonal antibody (to detect MHM2 PrP) (Kascsak, R. J., et al. Mouse polyclonal and monoclonal antibody to scrapie-associated fibril proteins. *J. ViroL* 61, 3688–3693 (1987)) at 1:5000 dilution in PBST overnight at 4° C. Following incubation with primary antibody, membranes were washed 3×10 min in PBST, incubated with horseradish peroxidase-labeled secondary antibody (Amersham Life Sciences) diluted 1:5000 in PBST for 30 to 60 min at 4° C. and washed again for 3×10 min in PBST. After chemiluminescent development with ECL reagent (Amersham) for 1 min, blots were sealed in plastic covers and exposed to ECL Hypermax film (Amersham). Films were processed automatically in a Konica film processor.

Example 1A

Branched polyamines inhibit formation of nascent $PrP^{Sc}$ and induce clearance of pre-existing $PrP^{Sc}$ Western blots were probed with 3F4 monoclonal antibody which recognizes newly expressed MHM2 PrP. ScN2a cells were exposed to SuperFect for 3 h and harvested 3 d after removal of SuperFect. Gells were run on both undigested, control sample and a sample subjected to limited proteolysis. The samples were run in separate lanes 1–6 with a control and limited proteolysis sample for each of the 6 lanes as follows: Lane 1: DOTAP-mediated transfection. Lane 2:30 μg/ml SuperFect, 5 μg pSPOX MHM2. Lane 3:75 μg/ml SuperFect, 5 μg pSPOX MHM2. Lane 4:150 μg/ml SuperFect, 5 μg pSOX MHM2. Lane 5:150 μg/ml SuperFect, 10 μg pSPOX MHM2. Lane 6: No addition of either transfection reagent or DNA. Forty μl of undigested brain homogenate was used in these studies while those samples subjected to limited digestion with proteinase K were concentrated 25-fold prior to SDS-PAGE. One ml of the digest were centrifuged at 100,000×g for 1 h at 4° C. and the pellets suspended in 80 μl of SDS sample buffer prior to SDS-PAGE followed by Western blotting. Apparent molecular weights based on migration of protein standards are 34.2, 28.3, and 19.9 kDa.

All of the control lanes 1–6 show multiple bands as expected. However, of the samples subjected to limited proteolytic only lane I shows bands. Unexpectedly, all of the partially digested sample lanes 2–5 show no bands and as expected no bands in the partially digested lane 6. These results show the effect of using SuperFect in clearing $PrP^{Sc}$.

Example 1B

The blot described above was stripped of antibody, exposed to labeled R073 and redeveloped. The antibody 3F4 used in Example 1 binds to $PrP^{C}$ but not to $PrP^{Sc}$. However, R073 binds to $PrP^{Sc}$ and $PrP^{C}$. Lanes 1, 2 and 3 show decreasing amounts of $PrP^{Sc}$ and lanes 4 and 5 show no detectable $PrP^{Sc}$.

Example 2A

Gels were run on undigested controls 1–4 and as above, samples subjected to limited proteolysis. The lanes were as follows: Lane 1: No SuperFect. Lane 2:30 μg/ml SuperFect. Lane 3:75 μg/ml SuperFect. Lane 4:150 μg/ml SuperFect. ScN2a cells were exposed to SuperFect for 3 h and harvested 3 d after removal of SuperFect. Apparent molecular weights based on migration of protein standards are 33.9, 28.8, and 20.5 kDa. In that each sample was tested after the same time period the results show the dose-dependent effect of SuperFect on $PrP^{Sc}$ removal. Lanes 1, 2 and 3 show decreasing amounts of $PrP^{Sc}$ and lane 4 shows no detectable $PrP^{Sc}$.

Example 2B

To determine the time-dependent effect of SuperFect three different panels with four lanes each were prepared and run as follows: ScN2a cells were exposed to 7.5 μg/ml: SuperFect (lanes 1–4), PEI (average molecular weight ~60,000) (lanes 5–8), or PAMAM, generation 4.0 (lanes 9–12). Time of exposure times for each polyamine: 0 hours (lanes 1, 5, and 9), 4 hours (lanes 2, 6, and 10), 8 hours (lanes 3, 7, and 11), 16 hours (lanes 4, 8, and 12). All samples were subjected to limited proteolysis to measure $PrP^{Sc}$. Apparent molecular weights based on migration of protein standards are 38, 26, and 15 kDa. Lanes of each of the three panels show decreasing amounts of $PrP^{Sc}$.

Example 3

In this example four panels A,B, C and D were created with panels having three double (control and test) lanes each. ScN2a cells were exposed to 1.5 μg/ml: (A) SuperFect, (B) PEI (average molecular weight ~60,000), (C) PAMAM, generation 4.0, or (D) no addition. Cells were harvested: Lane 1, before addition; Lane 2, immediately following 1 week continuous exposure to test compounds; and Lane 3, three weeks after removal of test compounds. Minus (−) symbol denotes undigested, control sample and plus (+) symbol designates sample subjected to limited proteolysis. Apparent molecular weights based on migration of protein standards are 33.9, 28.8, and 20.5 kDa. Test lanes 3 in panel A showed slight $PrP^{Sc}$ after three weeks and test lanes 3 in panels B and C showed no detectable $PrP^{Sc}$ whereas $PrP^{Sc}$ was present in all lanes in panel D.

Example 4A

Four separate gels were run to demonstrate the effect of adding chloroquine would have on $PrP^{Sc}$ levels. The lanes 1 control and 3 where chloroquine was added show clear bands for $PrP^{Sc}$ whereas lanes 2 and 4 with no chloroquine show barely detectable amounts of $PrP^{Sc}$. The four lanes were prepared as follows: ScN2a cells were treated Lane 1: Control media. Lane 2:7.5 μg/ml PEI (average molecular weight ~60,000). Lane 3: PEI plus 100 μM chloroquine. Lane 4: PEI plus 30 μM $NH_4Cl$. Chloroquine and $NH_4Cl$ were added 1 h prior to addition of PEI. Cells were harvested 16 hours after addition of PEI. All samples shown were subjected to limited proteolysis to measure $PrP^{Sc}$. Apparent molecular weights based on migration of protein standards are 38, 26, and 15 kDa.

Example 4B

Eight lanes with SuperFect (+SF) and eight lanes without SuperFect (−SF) were prepared. Lanes 1–8 of each group had an adjusted pH of 3.6, 4, 5, 6, 7, 8, 9 and 9.6. In vitro mixture of crude mouse brain homogenates with SuperFect under a range of pH conditions was performed as described in methods (measured final pH of each sample denoted above the lanes). Addition of 60 μg/ml SuperFect denoted as "+SF" and control with no addition as "−SF". All samples shown were subjected to limited proteolysis to measure $PrP^{Sc}$. Apparent molecular weights based on migration of protein standards are 30 and 27 kDa. All lanes of the −SF group showed $PrP^{Sc}$ present. Lanes 3–8 of the +SF group showed $PrP^{Sc}$. However, lanes 1 and 2 with respective pH levels of 3.6 and 4.0 showed very slight detectable $PrP^{Sc}$. The results show that the ability of a blanched polycation such as SuperFect to clear $PrP^{Sc}$ is pH dependent.

Example 5

Sixteen different lanes were prepared as described. Lanes 1 and 2 were control lanes and each of lanes 3–16 contained a different compound as tested in Table 1. The test compounds were all polyamines. Thus, the results show removal of $PrP^{Sc}$ from brain homogenate in vitro by various polyamines. Samples were incubated with polyamines at pH 3.6 and processed as described in Methods. Each polyamine was tested at 60 μg/ml concentration. Lanes 1 and 2: control. Lane 3: poly-(L)lysine. Lane 4: PAMAM, generation 0.0. Lane 5: PAMAM, generation 1.0. Lane 6: PAMAM, generation 2.0. Lane 7: PAMAM, generation 3.0. Lane 8: PAMAM, generation 4.0. Lane 9: PAMAM-OH, generation 4.0. Lane 10: PPI, generation 2.0. Lane 11: PPI, generation 4.0. Lane 12: linear PEI. Lane 13: high MW PEI. Lane 14: low MW PEI. Lane 15: average MW PEI. Lane 16: SuperFect. All samples shown were subjected to limited proteolysis to measure $PrP^{Sc}$. Apparent molecular weights based on migration of protein standards are 30 and 27 kDa. Table 1. Removal of $PrP^{Sc}$ by polymer compounds. $IC_{50}$= approximate concentration of polymer required to reduce $PrP^{Sc}$ to 50% of control levels in ScN2a cells after exposure for 16 hours. All compounds were tested at 5 different concentrations. $PrP^{Sc}$ levels were measured by densitometry of Western blot signals.

TABLE 1

(Note that Table 1 includes information on the characteristics of compounds used but that the list does not correspond directly to lanes 1–16)

| Compound | Molecular Weight | Primary $NH_2$ groups | $IC_{50}$ (ng/ml) |
| --- | --- | --- | --- |
| PAMAM generation 0.0 | 517 | 4 | >10,000 |
| PAMAM generation 1.0 | 1,430 | 8 | >10,000 |
| PAMAM generation 2.0 | 3,256 | 16 | 2,000 |
| PAMAM generation 3.0 | 6,909 | 32 | 400 |

TABLE 1-continued (Note that Table 1 includes information
on the characteristics of compounds used but that
the list does not correspond directly to lanes 1–16)

| Compound | Molecular Weight | Primary NH$_2$ groups | IC$_{50}$ (ng/ml) |
|---|---|---|---|
| PAMAM generation 4.0 | 14,215 | 64 | 80 |
| PAMAM-OH generation 4.0 | 14,279 | 0 | >10,000 |
| PPI generation 2.0 | 773 | 8 | 2,000 |
| PPI generation 4.0 | 3,514 | 32 | 80 |
| Low MW PEI | ~25,000 | | 2,000 |
| Average MW PEI | ~60,000 | | 400 |
| High MW PEI | ~800,000 | | 80 |
| Linear PEI | ~60,000 | | 2,000 |
| poly-(L)lysine | ~60,000 | >500 | 10,000 |
| SuperFect | | | 400 |

Lanes 7, 8, 11 and 13 showed the best results, i.e. best ability to clear PrP$^{Sc}$ under these conditions. Specifically, PAMAM generation 4.0 in lane 8 showed the best ability to clear PrP$^{Sc}$ under these conditions whereas PAMAM-OH generation 4.0 showed almost no detectable ability to clear PrP$^{Sc}$ and was comparable to the control.

Example 6

Transfection of PrP$^{Sc}$ Expressing Cells with Dendrimer Compounds

Cells of neuronal origin expressing PrP$^{Sc}$ were examined for the ability of compounds to suppress PrP$^{Sc}$ formation.

Transfection Studies

Stock cultures of N2a and ScN2a cells were maintained in MEM with 10% FBS, 10% Glutamax (Gibco BRL), 100 U penicillin, and 100 μg/ml streptomycin. Cells from a single confluent 100 mm dish were trypsinized and split into 10 separate 60 mm dishes containing DME plus 10% FBS, 10% Glutamax, 100 U penicillin, and 100 μg/ml streptomycin (supplemented DME) one day prior to transfection. Immediately prior to transfection, the dishes were washed twice with 4 ml supplemented DME media and then drained.

For DOTAP-mediated transfection, 15 μg pSPOX MHM2 was resuspended in 150 μl sterile Hepes Buffered Saline (HBS) on the day of transfection. The DNA solution was then mixed with an equal volume of 333 μg/ml DOTAP (Boehringer Mannheim) in HBS in Falcon 2059 tubes and incubated at room temperature for 10 minutes to allow formation of DNA/lipid complexes. Supplemented DME (2.5 ml) was added to the mixture, and this was then pipetted onto drained cell monolayers. The following day, the medium containing DNA/lipid was removed and replaced with fresh supplemented DME. Cells were harvested three days later.

For Superfect™-mediated transfections/exposures, Superfect™ with or without DNA was added to 1 ml supplemented DME in a Falcon 2059 tube to achieve the specific concentrations needed for each experiment. This mixture was pipetted up and down twice and then onto drained cell monolayers. After exposure for the indicated times, the medium containing Superfect™ was removed and replaced with fresh supplemented DME. Cells were harvested at specified times after removal of Superfect™.

Exposures to PPI (DAB-Am-8, Polypropylenimine octaamine Dendrimer, Generation 2.0 Aldrich 46,072–9), Intact PAMAM (Starburst (PAMAM)Dendrimer, Generation 4. Aldrich 41,244–9), PEI (Sigma), poly-(L)lysine (Sigma), and poly-(D) lysine (Sigma) were performed as described above for Superfect™.

Isolation of Protein from Treated Cells

Cells were harvested by lysis in 1.2 ml of 20 mM Tris pH 8.0 containing 100 mM NaCl, 0.5% NP-40, and 0.5% sodium deoxycholate. Nuclei were removed from the lysate by centrifugation at 2000 rpm for 5 min. This lysate typically had a protein concentration of 0.5 mg/ml measured by the BCA assay. For samples not treated with proteinase K, 40 μl of whole lysate (representing 20 μg total protein) was mixed with 40 μl of 2×SDS sample buffer. For proteinase K digestion, 1 ml of lysate was incubated with 20 μg/ml proteinase K (total protein:enzyme ratio =25:1) for 1 hr at 37° C. Proteolytic digestion was terminated by the addition of 8 μl of 0.5M PMSF in absolute ethanol. Samples were then centrifuged for 75 min in a Beckman TLA-45 rotor at 100,000×g at 4° C. The pellet was resuspended by repeated pipetting in 80 μl of 1×SDS sample buffer. The entire sample (representing 0.5 mg total protein before digestion) was loaded for SDS-PAGE.

Western Blot Analysis

Immunoreactive PrP bands from the DOTAP-mediated transfection were detected before and after digestion with proteinase K with monoclonal antibody 3F4. The construct used to express PrP$^{Sc}$ in the ScN2a cells is MHM2 a chimeric construct that differs from wild-type (wt) MoPrP at positions 108 and 111 (Scott et al., (1992) *Protein Sci.* 1:986–997). Substitution at these positions with the corresponding residues (109 and 112 respectively) from the Syrian hamster (SHa) PrP sequence creates an epitope for 3F4 (Kascsak et al., (1987) *J. Virol.* 61:3688–3693), which does not recognize endogenous wt MoPrP in ScN2a cells and hence facilitates specific detection of the transgene by Western blot.

Following electrophoresis, Western blotting was performed as previously described (Scott et al., (1989) *Cell* 59:847–857). Samples were boiled for 5 minutes and cleared by centrifugation for 1 minute at 14,000 rpm in a Beckman ultrafuge. SDS-PAGE was carried out in 1.5 mm, 12% polyacrylamide gels (Laemmli (1970) *Nature* 227:661–665). Membranes were blocked with 5% nonfat milk protein in PBST (calcium- and magnesium-free PBS plus 0.1% Tween 20) for 1 hour at room temperature. Blocked membranes were incubated with primary RO73 polyclonal or 3F4 monoclonal antibody at a 1:5000 dilution in PBST overnight at 4° C.

Following incubation with primary antibody, membranes were washed 3×10 minutes in PBST, incubated with horseradish peroxidase-labeled secondary antibody (Amersham Life Sciences) diluted 1:5000 in PBST for 25 minutes at room temperature and washed again for 3×10 minutes in PBST. After chemiluminescent development with ECL reagent (Amersham) for 1 minute, blots were sealed in plastic covers and exposed to ECL Hypermax film (Amersham). Films were processed automatically in a Konica film processor.

In contrast to DOTAP-transfected cells, ScN2a cells transfected with varying concentrations of Superfect™ and DNA did not appear to contain protease-resistant MHM2. Close scrutiny revealed that, prior to protease digestion, Superfect™-transfected samples express MHM2 bands which are not seen in the background pattern of the control sample. These observations indicate that MHM2 PrP was successfully expressed using Superfect™ transfection reagent, but conversion of MHM2 PrP$^C$ to protease-resistant MHM2 PrP$^{Sc}$ was inhibited by Superfect™.

To examine whether Superfect™ had affected levels of preexisting PrP$^{Sc}$ in ScN2a cells, the Western blot probed with 3F4 antibody was reprobed with polyclonal antibody RO73, which is able to recognize endogenous MoPrP. Remarkably, Superfect™ caused the disappearance of preexisting MoPrP$^{Sc}$ from ScN2a cells in a dose-dependent manner. After treatment with Superfect™, PrP$^{Sc}$ could not be detected in the nuclear fraction, pellet, supernatant, or media. The concentration of Superfect™ required to fully remove preexisting PrP$^{Sc}$ with a three hour exposure was 300 μg/ml, whereas 30 μg/ml was sufficient to interfere with the formation of new MHM2 PrP$^{Sc}$ within the same time frame.

Length of exposure dramatically influenced the ability of Superfect™ to remove PrP$^{Sc}$ from ScN2a cells. Whereas a 3 hour exposure to 150 μg/ml Superfect™ significantly lowered PrP$^{Sc}$ levels in ScN2a cells, exposure for 10 min to the same dose of Superfect™ did not affect PrP$^{Sc}$ levels. When ScN2a cells were exposed to 2 μg/ml Superfect™ continuously for 1 week, PrP$^{Sc}$ disappeared completely.

The conditions tested did not appear to be toxic for the cells. Neither 150 μg/ml Superfect™ for 3 hrs nor 2 μg/ml Superfect™ continuously for 1 week caused any obvious changes in cell morphology, viability, or growth as judged by phase contrast microscopy.

Example 7

Elimination of PrP$^{Sc}$ by repeated exposures to Superfect™

The duration in the reduction in PrP$^{Sc}$ levels after exposure to Superfect™ was examined, and it was shown that this reduction could persist for extended periods after removal of Superfect™. Following the exposure of ScN2a cells to a single dose of 150 μg/ml Superfect™ for 3 hrs, PrP$^{Sc}$ levels remained low for one week, but returned to near baseline levels after 3 weeks in culture without Superfect™.

In contrast, when ScN2a cells were exposed to 4 separate doses of Superfect™ over the course of 16 days, very little PrP$^{Sc}$ could be detected 4 weeks after the final exposure to Superfect™. This result offers hope that prolonged exposure to Superfect™ may lead to long term cure of scrapie infection in cultured cells.

Example 8

Superfect™ does not destroy PrP$^{Sc}$ directly

The dendrimer Superfect™ was used to determine if it could exert a similar inhibitory effect on PrP$^{Sc}$ in either crude brain homogenates or purified PrP 27–30 rods. Brain homogenates from normal and scrapie-affected Syrian hamsters (10% (w/v) in sterile PBS) were prepared by repeated extrusion through syringe needles of successively smaller size, from 18 to 22 gauge. Nuclei and debris were removed by centrifugation at 1000×g for 10 min. The bicinchoninic acid (BCA) protein assay (Pierce) was used to determine protein concentration. Homogenates were adjusted to 10 mg/ml protein with PBS and 50 μl was added to 450 μl of lysis buffer containing 100 mM NaCl, 1 mM EDTA, 0.55% sodium deoxycholate, 0.55% Triton X-100, and 50 mM Tris-HCl pH 7.5. This mixture was then incubated with 0–300 μg/ml Superfect™ for 3 hrs at 37 ° C. and then centrifuged for 10 min at 14,000 rpm in a Beckman Ultrafuge. The pellet was resuspended in 450 μl lysis buffer without Superfect™. Proteinase K (Boehringer Mannheim) was added to achieve a final concentration of 20 μg/ml, and thus the ratio of total protein/enzyme was 50:1. Samples were incubated for 1 h at 37 ° C. Proteolytic digestion was terminated by the addition of 8 μl of 0.5 M PMSF in ethanol. Samples were then centrifuged for 75 min in a Beckman TLA-45 rotor at 100,000×g at 4 ° C. Undigested samples (10 μl) were mixed with an equal volume of 2×SDS sample buffer. For digested samples, the pellet was resuspended by repeated pipetting in 100 μl 1×SDS sample buffer. Twenty μl (equivalent to 100 μg of total protein prior to proteinase K digestion) of each sample was loaded for SDS-PAGE.

PrP 27–30 rods were purified from scrapie-affected Syrian hamster brains and previously described (Prusiner et al., (1983) Cell 35:349–358). Purified rods (3.5 μg/ml) were incubated with or without 900 μg/ml Superfect™ in 100 μl supplemented DME. After 16 hrs at 37° C., the suspension was centrifuged at 100,000×g at 4° C. The pellet was resuspended in 500 μl of buffer containing 1 mg/ml BSA, 100 mM NaCl, 1 mM EDTA, 0.55% sodium deoxycholate, 0.55% Triton X-100, and 50 mM Tris-HCl pH 7.5. Proteinase K was added to achieve a final concentration of 20 μg/ml. Samples were incubated for 1 h at 37° C.

Proteolytic digestion was terminated by the addition of 8 μl of 0.5 M Pefabloc (Boehringer Mannheim). Samples were then centrifuged for 75 min at 1000,000×g at 4° C. Undigested samples (50 μl) were mixed with an equal volume of 2×SDS sample buffer. For digested samples, the pellet was resuspended by repeated pipetting in 100 μl 1×SDS sample buffer. Forty μl of each sample was loaded for SDS-PAGE.

When Superfect™ was mixed with either crude homogenates of scrapie-affected Syrian hamsters or with purified Syrian hamster PrP 27–30, there was no significant change in the level of proteinase K-resistant PrP$^{Sc}$. These results suggest that the removal of PrP$^{Sc}$ from ScN2a cells by Superfect™ depends on the presence of intact cellular machinery.

Example 9

Clearance of PrP$^{Sc}$ levels by other dendritic polycations

The Superfect™ compound is a high molecular weight component of heat-degraded PAMAM Starburst dendrimers, which is a cationic, highly-branched, monodisperse polymers (Tang et al., (1996) Bioconjugate Chem. 7:703–714). To identify other potentially useful anti-prion therapeutic agents, we screened three other dendritic polycations and two linear cationic polymers for their ability to clear PrP$^{Sc}$ from ScN2a cells. Among the dendritic macromolecules tested, polyetheleneimine (PEI) was the most potent, removing the majority of PrP$^{Sc}$ from ScN2a cells after 3 hrs when used at a concentration of 10 μg/ml. Intact PAMAM displayed a potency comparable to Superfect™, removing approximately half of the detectable PrP$^{Sc}$ when used at a concentration of 50 μg/ml. In contrast, the dendrimer polypropyleneimine (PPI), poly-(L)lysine, and the linear polycation poly-(D)lysine failed to reduce PrP$^{Sc}$ levels at concentrations between 10–50 μg/ml. These results demonstrate that a branched polymeric architecture is required to clear PrP$^{Sc}$. Furthermore, exposure of ScN2a cells to either PEI or intact PAMAM for one week at a concentration of 1.5 μg/ml completely removes PrP$^{Sc}$, effectively curing the cells of scrapie infection.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A food composition for preventing PrP$^{Sc}$ formation in an animal, said composition comprising:

a therapeutically effective amount of an active composition comprising an unconjugated dendritic polycation and an acid in an amount sufficient to maintain a pH of about less than 6; and a food;

wherein the active composition is present in an amount effective to prevent $PrP^{Sc}$ formation.

2. The food composition of claim 1, wherein the food composition is meat.

3. The food composition of claim 1, wherein the pH is less than 5 and wherein at least one branch of the dendritic polycation is positively charged.

4. The food composition of claim 3, wherein the dendritic polycation is selected from the group consisting of polypropylene imine, polyethyleneimine (PEI) poly(4'-aza-4'-methylheptamethylene D-glucaramide), and polyamidoamine.

5. The food composition of claim 1, wherein the pH is maintained at 4.5 or less.

6. The food composition of claim 1, wherein the food is human food.

7. The food composition of claim 6, wherein the human food is a meat selected from the group consisting of beef and mutton.

8. The food composition of claim 2, wherein the meat is a ground meat product.

9. The food composition of claim 1, wherein the acid is a liquid.

10. The food composition of claim 9, wherein the liquid acid comprises vinegar.

11. The food composition of claim 9, wherein the liquid acid comprises oil extracted from a pepper plant.

* * * * *